(12) United States Patent
Sacurai et al.

(10) Patent No.: US 8,268,831 B2
(45) Date of Patent: Sep. 18, 2012

(54) COMPOUNDS DERIVED FROM 2-(3-METHYLENEDIOXY)-BENZOYL INDOL

(75) Inventors: Sérgio Luiz Sacurai, São Paulo (BR); Carlos Eduardo Da Costa Touzarim, São Paulo (BR); Marcio Henrique Zaim, São Paulo (BR)

(73) Assignee: Biolab Sanus Farmaceutica Ltda., Taboao da Serra (BR)

( * ) Notice: Subject to any disclaimer, the term of this patent is extended or adjusted under 35 U.S.C. 154(b) by 0 days.

(21) Appl. No.: 13/121,650

(22) PCT Filed: Sep. 30, 2009

(86) PCT No.: PCT/BR2009/000300
§ 371 (c)(1),
(2), (4) Date: Mar. 29, 2011

(87) PCT Pub. No.: WO2010/037190
PCT Pub. Date: Apr. 8, 2010

(65) Prior Publication Data
US 2011/0195976 A1    Aug. 11, 2011

(30) Foreign Application Priority Data
Sep. 30, 2008    (BR) ..................................... 0804119

(51) Int. Cl.
*A61K 31/496* (2006.01)
*C07D 405/14* (2006.01)

(52) U.S. Cl. .................................. 514/254.09; 544/373
(58) Field of Classification Search ............. 514/254.09; 544/373; 548/454
See application file for complete search history.

(56) References Cited

FOREIGN PATENT DOCUMENTS

| WO | WO 97/03675 A1 | 2/1997 |
|---|---|---|
| WO | WO 02/098877 A1 | 12/2002 |
| WO | WO 2010/035304 A2 | 4/2010 |

OTHER PUBLICATIONS

Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*

* cited by examiner

*Primary Examiner* — Kristin Bianchi
(74) *Attorney, Agent, or Firm* — Arent Fox LLP

(57) ABSTRACT

The present invention describes a series of derivatives of 2-(3-methylenedioxy)-benzoyl indol, their mixtures, their pharmaceutically acceptable salts, their enantiomers, pharmaceutical compositions comprising them, processes for preparing them, use in the prophylactic and/or curative treatment of sexual dysfunction. More specifically, the invention describes derivatives (R)-3-((2-(benzo[d][1,3]dioxol-5-carbonyl)-1H-indol-3-yl)methyl)-1-methylpiperazine-2,5-dione, and S)-3-((2-(benzo[d][1,3]dioxol-5-carbonyl)-1H-indol-3-yl)methyl)-1-methylpiperazine-2,5-dione.

9 Claims, 2 Drawing Sheets

COMPOUNDS DERIVED FROM 2-(3-METHYLENEDIOXY)-BENZOYL INDOL

CROSS-REFERENCED TO RELATED APPLICATION

This application is a National Stage entry of International Application No. PCT/BR2009/000300, filed on Sept. 30, 2009, which claims priority to Brazilian Patent Application PI0804119-9, filed on Sept. 30, 2008. The disclosure of the prior application is herby incorporated in its entirety by reference.

FIELD OF INVENTION

The present invention describes a series of derivatives of 2-(3-methylenedioxy)-benzoyl indol, their mixtures in any ratio, their pharmaceutically acceptable salts, their enantiomers, pharmaceutical compositions comprising them, processes for preparing them and their intermediates, and their uses in the prophylactic and/or curative treatment of sexual dysfunction. More specifically, the present invention describes the derivatives (R)-3-((2-(benzo[d][1,3]dioxol-5-carbonyl)-1H-indol-3-yl)methyl)-1-methylpiperazine-2,5-dione and (S)-3-((2-(benzo[d][1,3]dioxol-5-carbonyl)-1H-indol-3-yl)methyl)-1-methylpiperazine-2,5-dione.

The present invention also describes a method of prophylactic and/or curative treatment for erectile dysfunction using derivatives of 2-(3-methylenedioxy)-benzoyl indol and, more particularly, the derivatives (R)-3-((2-(benzo[d][1,3]dioxol-5-carbonyl)-1H-indol-3-yl)methyl)-1-methylpiperazine-2,5-dione, and its enantiomer (S)-3-((2-(benzo[d][1,3]dioxol-5-carbonyl)-1H-indol-3-yl)methyl)-1-methylpiperazine-2,5-dione.

The present invention also describes these compounds and their mixtures in any ratio, their pharmaceutically acceptable salts, pharmaceutical compositions comprising them, and their uses as stimulators of NO expression in tissues, and selective inhibitors of the enzyme phosphodiesterase, in particular phosphodiesterase type 5 (PDE-5).

BACKGROUND OF THE INVENTION

Before the appearance of the first oral treatment, male sexual impotence was treated by means of intracavernous injections and other methods, due to, in particular, innumerous concerns on the adverse reactions that oral route administration would be able to cause in humans. Papaverine and pentoxifylline, for example, were used in the treatment of erectile dysfunction by intracavernous injections. Other methods of treatment, less efficient, were, for example, psychological therapies and surgical implants.

The treatment by oral route is more acceptable by man and it emerged from clinical studies using specific inhibitors to cGMP, PDE, and more specifically, PDE-5. The predecessor of these compounds was 5-[2-Ethoxy-5-(4-methylpiperazinylsulphonyl)phenyl]-1-methyl-3-n-propyl-1,6-dihydro-7H-pyrazol[4,3-d]pyrimidin-7-one, or sildenafil, with vasodilator properties and potentiator properties of Endothelium Derived Relaxing Factor (EDRF) and nitrovasodilators. Sildenafil is the active principle of the medicament Viagra®.

Later, other PDE-5 inhibitor compounds were developed and described in various publications of specialized literature, and in patent publications. The most well-known are vardenafil, the active principle of the medicament Levitra®, and tadalafil, the active principle of the medicament Cialis®.

Another class of PDE-5 inhibitor compounds is described in the publication WO 03/000691. Therein are disclosed a series of compounds derived from β-carboline, which are prepared from compounds of formula (a) and (b) below, disclosed, respectively, in U.S. Pat. Nos. 6,117,881 and 5,859,006.

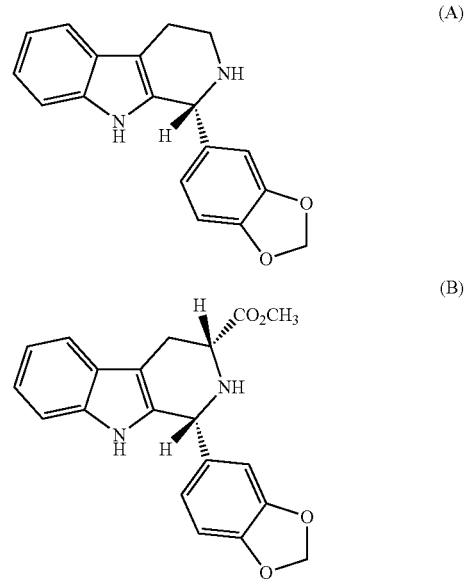

The compounds of the present invention, derivatives of 2-(3-methylenedioxy)-benzoyl indol, can be utilized in treatment of sexual dysfunction, and in one embodiment, can be utilized as stimulators of NO expression in tissues, and in another embodiment, can be utilized as selective inhibitors of the enzyme phosphodiesterase, in particular phosphodiesterase type 5 (PDE-5).

DESCRIPTION OF THE INVENTION

The present invention provides new compounds derived from 2-(3-methylenedioxy)-benzoyl indol, their mixtures, their pharmaceutically acceptable salts, their isomers and pharmaceutical compositions comprising them, which are effective in the prophylactic and/or curative treatment of sexual dysfunction and/or erectile dysfunction. In one embodiment, the compounds possess vasodilator and muscle relaxing properties, in another embodiment, the compounds stimulate NO expression in tissues, and in another embodiment, the compounds selectively inhibit phosphodiesterase, in particular phosphodiesterase type 5 (PDE-5). Preferentially, the new compounds derived from 2-(3-methylenedioxy)-benzoyl indol are derivatives (R)-3-((2-(benzo[d][1,3]dioxol-5-carbonyl)-1H-indol-3-yl)methyl)-1-methylpiperazine-2,5-dione, its enantiomer (S)-3-((2-(benzo[d][1,3]dioxol-5-carbonyl)-1H-indol-3-yl)methyl)-1- methylpiperazine-2,5-dione, and mixtures thereof in any ratio.

The present invention also provides processes for preparing the derivatives of 2-(3-methylenedioxy)-benzoyl indol and their mixtures, and more specifically, derivatives (R)-3-((2-(benzo[d][1,3]dioxol-5-carbonyl)-1H-indol-3-yl)methyl)-1-methylpiperazine-2,5-dione, its enantiomer (S)-3-((2-(benzo[d][1,3]dioxol-5-carbonyl)-1H-indol-3-yl)methyl)-1-methylpiperazine-2,5-dione, and mixtures thereof in any ratio.

In some aspects, the present invention provides pharmaceutical compositions comprising as active ingredient an effective amount of one or more derivatives of 2-(3-methylenedioxy)-benzoyl indol, their mixtures in any ratio or their pharmaceutical acceptable salts, and pharmaceutically acceptable excipients. More specifically, the active ingredient is the derivative (R)-3-((2-(benzo[d][1,3]dioxol-5-carbonyl)-1H-indol-3-yl)methyl)-1-methylpiperazine-2,5-dione, its enantiomer (S)-3-((2-(benzo[d][1,3]dioxol-5-carbonyl)-1H-indol-3-yl)methyl)-1-methylpiperazine-2,5-dione, or mixtures thereof in any ratio.

In some aspects, the present invention provides a medicament comprising as active ingredient a therapeutically effective quantity of one or more derivatives of 2-(3-methylenedioxy)-benzoyl indol, their mixtures in any ratio or their pharmaceutically acceptable salts. More specifically, said medicaments contain as active ingredient the derivative (R)-3-((2-(benzo[d][1,3]dioxol-5-carbonyl)-1H-indol-3-yl)methyl)-1-methylpiperazine-2,5-dione, its enantiomer (S)-3-((2-(benzo[d][1,3]dioxol-5-carbonyl)-1H-indol-3-yl)methyl)-1-methylpiperazine-2,5-dione, or mixtures thereof in any ratio.

In another aspect, the present invention provides the use of the derivatives 2-(3-methylenedioxy)-benzoyl indol, their mixtures in any ratio or their pharmaceutical acceptable salts, for the curative and/or prophylactic treatment, by oral route, of erectile and/or sexual dysfunction in man. More specifically, the derivative 2-(3-methylenedioxy)-benzoyl indol is the derivative (R)-3-((2-(benzo[d][1,3]dioxol-5-carbonyl)-1H-indol-3-yl)methyl)-1-methylpiperazine-2,5-dione, and/or its enantiomer (S)-3-((2-(benzo[d][1,3]dioxol-5-carbonyl)-1H-indol-3-yl)methyl)-1-methylpiperazine-2,5-dione.

DETAILED DESCRIPTION OF THE INVENTION

Figure 1:
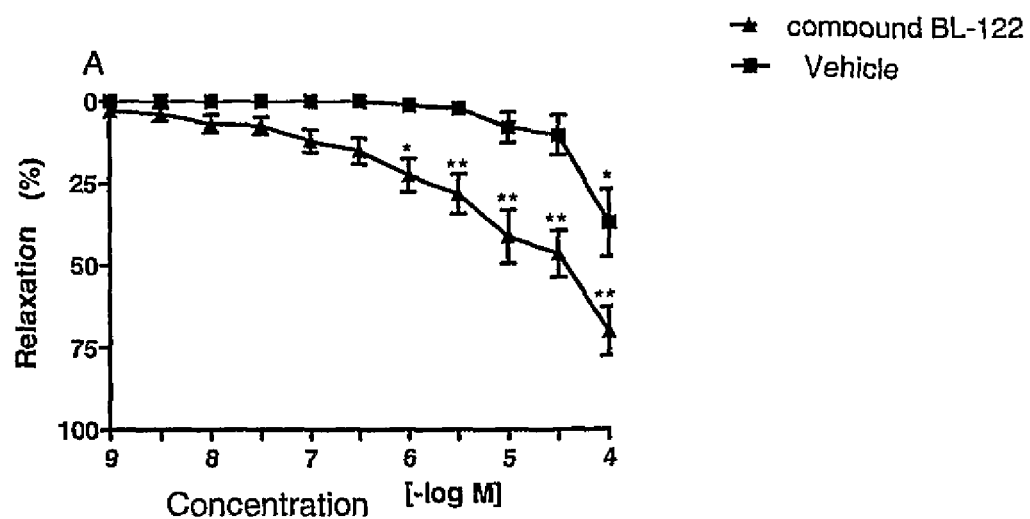
FIG. 1—dose response curve of the relaxing effect of compound BL-122 (a) and vehicle (b) on isolated cavernous body of rabbit. The values represent the average±SEM of 8 preparations, obtained from 6 animals. The asterisks indicate the level of significance *P<0.05, **P<0.01, compared with the cavernous body with 0% of initial relaxation, after previous contraction by Phenylephrine (3-10 µM) corresponding to 1.7±0.07 g of tension.

The present invention provides derivatives of 2-(3-methylenedioxy)-benzoyl indol with structures of formula (I)

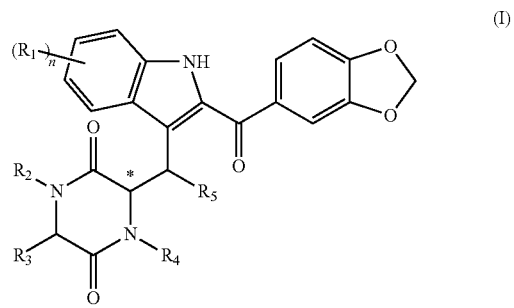

their salts and solvates, such as hydrates, wherein:

$R^1$ represents hydrogen, halogen, $C_{1-6}$ alkyl or O—R', where R' represents hydrogen or a lower alkyl;

n represents a number from 0 to 4;

$R^2$ represents hydrogen, $C_{1-6}$ alkyl, $C_{2-6}$ alkenyl, $C_{2-6}$ alkynyl, halo$C_{1-6}$alkyl, $C_{3-8}$ cycloalkyl, $C_{3-8}$ cycloalkyl$C_{1-3}$ alkyl, aryl $C_{1-3}$ alkyl or heteroaryl $C_{1-3}$ alkyl;

$R^3$ represents hydrogen, or $C_{1-3}$ alkyl or $R^2$ and $R^3$ together represent 3- or 4-substituents of a alkyl or alkenyl ring;

$R^4$ represents hydrogen, $C_{1-6}$ alkyl, $C_{2-6}$ alkenyl, $C_{2-6}$ alkynyl, halo$C_{1-6}$alkyl, $C_{3-8}$ cycloalkyl, $C_{3-8}$ cycloalkyl$C_{1-3}$ alkyl, aryl $C_{1-3}$ alkyl or heteroaryl $C_{1-3}$ alkyl;

$R^5$ represents hydrogen or O—R', where R' represents hydrogen or a lower alkyl.

For $R^2$ and $R^4$, the term "aryl" of the group aryl $C_{1-3}$ alkyl, represents a phenyl or substituted phenyl with one or more halogens (for example, 1, 2, or 3) or $C_{1-6}$ alkyl, $C_{1-6}$ alkoxy or methylenedioxy. "The heteroaryl" term of the heteroaryl $C_{1-3}$ alkyl group, represents a furil or pyridyl group, optionally substituted with one or more halogens, $C_{1-6}$ alkyl or $C_{1-6}$ alkoxy. The term "$C_{3-8}$ cycloalkyl" of the group $C_{3-8}$ cycloalkyl $C_{1-3}$ alkyl, represents a monocyclic ring containing 3 to 8 carbon atoms. Examples of cycloalkyl rings include $C_{3-6}$ cycloalkyl rings: cyclopropyl, cyclobutyl, cyclopentyl and cyclohexyl.

In the above definitions, the term "alkyl" term represents a main alkyl chain or a branched alkyl chain from the represented groups. For example, the $C_{1-4}$ alkyl represents: methyl, ethyl, n-propyl, i-propyl, n-butyl, s-butyl and t-butyl. The tem "alkenyl" used in the above definitions includes straight and branched-chain alkenyl groups, such as vinyl and allyl. The term "alkynyl" used in the above definitions includes straight and branched-chain alkynyl groups, such as acetylene. The term "halogen" represents atoms of fluorine, chlorine, bromine or iodine. The term "halo$C_{1-6}$alkyl" correspond to an alkyl group as defined above, containing one to six carbon atoms, substituted with one or more atoms of halogen, for example 1, 2 or 3.

When $R^1$ represents a halogen atom or an O—R' group or a $C_{1-6}$ alkyl group, this substituent can be bonded in any position available on the phenyl of the indol and in more than one position.

The compounds of formula (I) can contain one or more asymmetrical centers, and so can exist as enantiomers and/or diastereoisomers. In particular, in the formula (I) above, a chiral center is indicated with an asterisk—hence, the invention includes individual enantiomers, and mixtures thereof.

The compounds of formula (I) can exist in different tautomeric forms and the invention includes individual tautomeric forms, and mixtures thereof.

The pharmaceutically acceptable salts of compounds of formula (I), which possess a basic center, can be formed by the addition of pharmaceutically acceptable acids. Some examples include salts of: hydrocloride, hydrobromide, sulphate or bisulphate, phosphate or hydrogen-phosphate, acetate, benzoate, succinate, fumarate, maleate, lactate, citrate, tartrate, gluconate, methanesulfonate, benzenesulfonate and p-toluenesulphonate. The compounds of formula (I) can be pharmaceutically acceptable metal salts, in particular salts of alkaline metals, with bases. For example, salts of sodium and potassium.

One particular group of compounds according to the present invention are compounds of formula (I) where $R^1$, $R^3$ and $R^4$ are hydrogen and $R^2$ is a $C_{1-6}$ alkyl group. More specifically, the derivatives (R)-3-((2-(benzo[d][1,3]dioxol-5-carbonyl)-1H-indol-3-yl)methyl)-1-methylpiperazine-2,5-dione and its enantiomer (S)-3-((2-(benzo[d][1,3]dioxol-5-carbonyl)-1H-indol-3-yl)methyl)-1-methylpiperazine-2,5-dione, respectively the compounds of formulas (Ib) and (Ic) below:

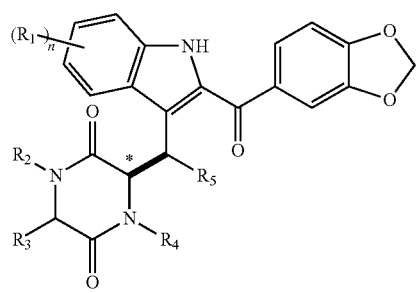

(Ib)

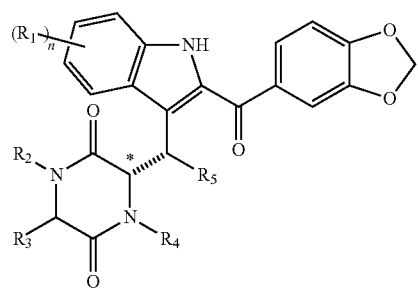

(Ic)

The present invention also describes intermediate compounds for the preparation of compounds of formula (I) defined above. Examples of these intermediate compounds are in formula (II):

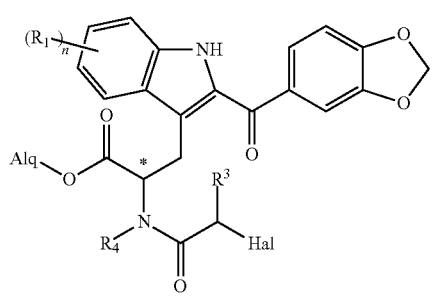

(II)

and their mixtures including racemic mixtures or salts or solvates thereof, where $R^1$, $R^3$ and $R^4$ are defined in claim 1, alq represents a $C_{1-6}$alkyl group and Hal represents a halogen atom.

Other examples of intermediate compounds are in formula (III):

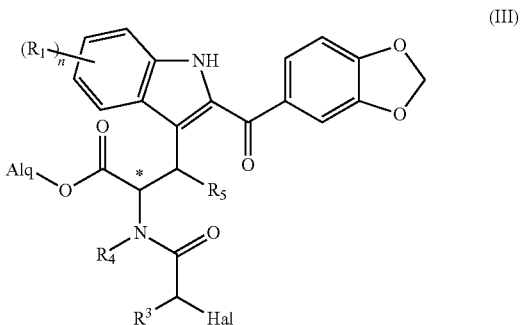

(III)

and their mixtures including racemic mixtures or salts or solvates thereof, where $R^1$, $R^2$, $R^3$, $R^4$, $R^5$, and n are defined in claim 1, alq represents a $C_{1-6}$alkyl group, and Hal represents a halogen atom.

The derivative (R)-3-((2-(benzo[d][1,3]dioxol-5-carbonyl)-1H-indol-3-yl)methyl)-1-methylpiperazine-2,5-dione, according to the invention can be prepared from (6R, trans)-6-(1,3-benzodioxol-5-yl)-2,3,6,7,12,12a-hexahydro-2-methyl-pirazino [1',2':1,6]pyrido[3,4-b]indol-1,4-dione, according to the reaction below (Procedure 1):

(Procedure 1)

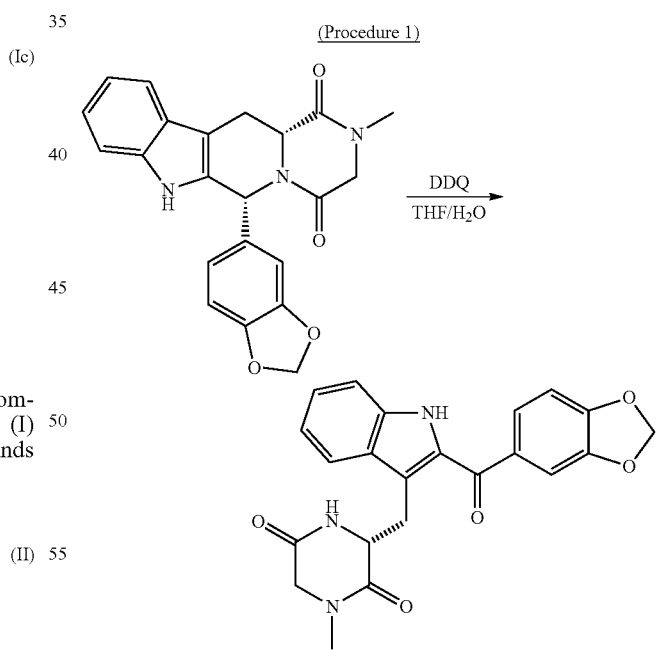

An alternative method for the preparation of the derivative (R)-3-((2-(benzo[d][1,3]dioxol-5-carbonyl)-1H-indol-3-yl)methyl)-1-methylpiperazine-2,5-dione, according to the present invention uses (6R, trans)-6-(1,3-benzodioxol-5-yl)-2,3,6,7,12,12a-hexahydro-2-methyl-pirazino [1',2':1,6]pyrido[3,4-b]indol-1,4-dione, according to the reaction below (Procedure 2):

(Procedure 2)

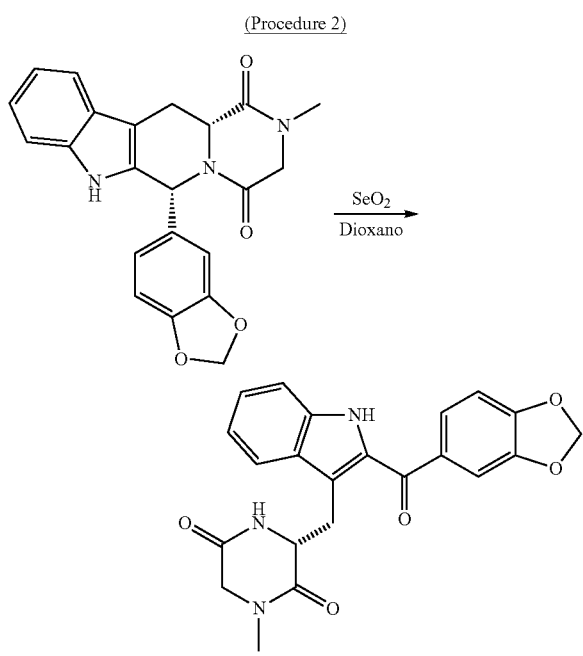

Further, the derivative (R)-3-((2-(benzo[d][1,3]dioxol-5-carbonyl)-1H-indol-3-yl)methyl)-1-methylpiperazine-2,5-dione, according to the present invention can be prepared using methyl (1R, 3R)-1-(benzo[d][1,3]dioxol-5-yl)-2-(2-chloroacetyl)-2,3,4,9-tetrahydro-1H-pyrido[3,4-b]indol-3-carboxylate, according to the reactions below (Procedure 3):

(Procedure 3)

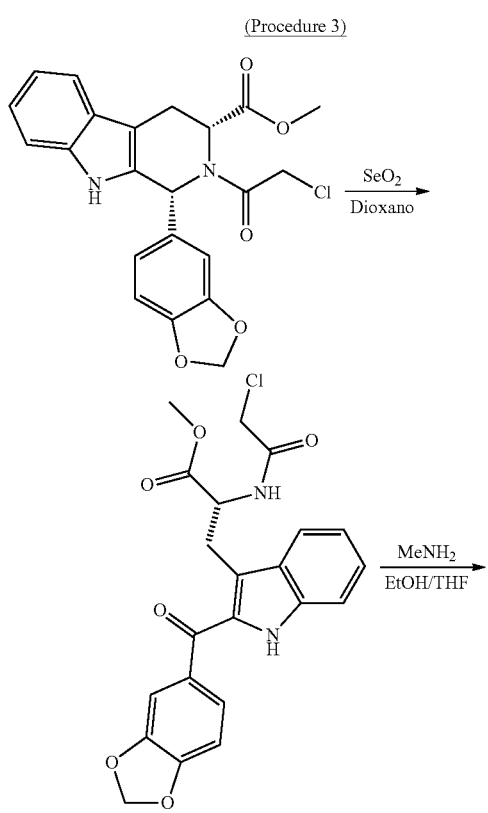

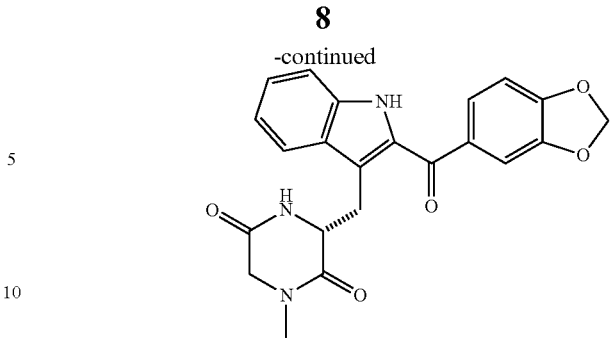

The enantiomer (S)-3-((2-(benzo[d][1,3]dioxol-5-carbonyl)-1H-indol-3-yl)methyl)-1-methylpiperazine-2,5-dione and a racemic mixture have been prepared using the procedures described above and using raw materials with the desired corresponding configuration for the product, and the reactions to which the raw materials were submitted did not alter the configuration of the desired asymmetrical center.

The following examples are non-limiting and more fully illustrate the invention, including processes for preparing compound (R)-3-((2-(benzo[d][1,3]dioxol-5-carbonyl)-1H-indol-3-yl)methyl)-1-methylpiperazine-2,5-dione, or compound BL-122, in accordance with procedures 1, 2 and 3 described above.

EXAMPLE 1

Procedure 1:

3.5 g of compound (6R, trans)-6-(1,3-benzodioxol-5-yl)-2,3,6,7,12,12a-hexahydro-2-methyl-pirazino[1',2':1,6]pyrido[3,4-b]indol-1,4-dione was mixed with 205 g of DDQ at room temperature. Afterwards, the mixture was added to 100 ml of the mixture THF:H$_2$O (9:1). The reaction mixture was kept under agitation for 8 hours at room temperature, being monitored for TLC. Additional DDQ was added until all the (6R, trans)-6-(1,3-benzodioxol-5-yl)-2,3,6,7,12,12a-hexahydro-2-methyl-pirazino[1',2':1,6]pyrido[3,4-b]indol-1,4-dione was consumed. After completion of the reaction, the mixture was washed with water and the product extracted with ethyl acetate. The organic phases were combined and dried with MgSO$_4$. The solvent was partially removed, leading to the precipitation of the product, which was filtered and dried in a 60° C. oven. The resulting product was a solid of white coloration (compound BL-122) and presented the following characteristics: p.f. 218-221° C. and $[\alpha]_D^{25}$=+12 (c 0.8; DMSO). RMN $^1$H (500 MHz-DMSO)=11.52 (1H, s); 7.95 (1H, d, J=3 Hz); 7.61 (1H, d, J=8 Hz); 7.43 (1H, d, J=8 Hz); 7.34 (1H, dd, J=8 Hz and J=1.5 Hz); 7.25-7.28 (2H, m); 7.07-7.10 (2H, m); 6.17 (2H, s); 4.00-4.03 (1H, m); 3.33-3.48 (3H, m); 2.98 (1H, d, J=17.5 Hz); 2.53 (3H, s).

EXAMPLE 2

Procedure 2:

1.4 g of selenium dioxide was added to a solution containing 2,4 g of (6R, trans)-6-(1,3-benzodioxol-5-yl)-2,3,6,7,12,12a-hexahydro-2-methyl-pirazino[1',2':1,6]pyrido[3,4-b]indol-1,4-dione and 60 ml of dioxane. The reaction mixture was kept under agitation and reflux for 4 hours. Afterwards, the reaction mixture was filtered on celite/silica and the solvent rotoevaporated. The solid product was recrystallized in CH$_2$Cl$_2$/MeOH and dried in a 60° C. oven. The resulting product was a solid of white coloration, compound BL-122, and presented the following characteristics: p.f. 219-221° C. and $[\alpha]_D^{25}$=+12 (c 0.8; DMSO). RMN $^1$H (500 MHz-DMSO)

=11.52 (1H, s); 7.95 (1H, d, J=3 Hz); 7.61 (1H, d, J=8 Hz); 7.43 (1H, d, J=8 Hz); 7.34 (1H, dd, J=8 Hz and J=1.5 Hz); 7.25-7.28 (2H, m); 7.07-7.10 (2H, m); 6.17 (2H, s); 4.00-4.03 (1H, m); 3.33-3.48 (3H, m); 2.98 (1H, d, J=17.5 Hz); 2.53 (3H, s).

EXAMPLE 3

Procedure 3:

32 g of selenium dioxide was added to a solution containing 107 g of methyl 1-(benzo[d][1,3]dioxol-5-yl)-2-(2-chloroacetyl)-2,3,4,9-tetrahydro-1H-pyrido[3,4-b]indol-3-carboxylate in 1250 ml of tetrahydrofuran (THF). The reaction mixture was kept under agitation and reflux for 1.5 hours. Afterwards, the reaction mixture was filtered on celite/silica and about 30% of the solvent was removed. To the reaction mixture was added 1000 ml of absolute ethanol and 200 ml of 30% methylamine in ethanol. This mixture was kept under reflux for hours. The solvent was partially removed, leading to precipitation of the final product, which was filtered and dried in a 60° C. oven. The resulting product was solid of white coloration, compound BL-122, and presented the following characteristics: p.f. 219-221° C. and $[\alpha]_D^{25}$=+12 (c 0.8; DMSO). RMN $^1$H (500 MHz-DMSO)=11.52 (1H, s); 7.95 (1H, d, J=3 Hz); 7.61 (1H, d, J=8 Hz); 7.43 (1H, d, J=8 Hz); 7.34 (1H, dd, J=8 Hz and J=1.5 Hz); 7.25-7.28 (2H, m); 7.07-7.10 (2H, m); 6.17 (2H, s); 4.00-4.03 (1H, m); 3.33-3.48 (3H, m); 2.98 (1H, d, J=17.5 Hz); 2.53 (3H, s); RMN $^{13}$C (125 MHz-DMSO)=186.9; 165.9; 164.8; 151.0; 147.4; 136.3; 132.9; 132.8; 127.5; 125.8; 124.9; 120.7; 119.8; 116.1; 112.6; 109.1; 108.0; 102.0; 55.7; 50.6; 33.0; 29.1.

The compounds of the present invention, as well as their pharmaceutically acceptable salts, are potential stimulators of NO expression in tissues, and potential inhibitors of PDE that are specific for cGMP. Thus, the compounds of formula (I) and their pharmaceutically acceptable salts are of interest in the therapy, specifically in treatment and prophylaxis, of a variety of conditions in which stimulation of NO expression in tissues, or inhibition of PDE that are specific for cGMP, are considered beneficial.

As a result of selective inhibition of PDE-5 by the compounds of the present invention, levels of cGMP are be elevated, which in turn, can promote the anti-platelet, anti-neutrophils, anti-vasospastic, vasodilatator, natriuretic and diuretic activities, as well as potentiation of the effects of the Endothelium Derived Relaxing Factor (EDRF), nitrovasodilatators, atrial natriuretic factor (ANF), brain natriuretic peptide (BNP), C-type natriuretic peptide (CNP) and endothelium-dependent relaxant agents, such as bradykinin, acetylcholine and 5-HT$_1$.

The compounds of formula (I) according to present invention have utility in the treatment and prevention of a large group of disorders, including stable, unstable and variant angina, hypertension, pulmonary hypertension, congestive heart failure, renal failure, arteriosclerosis, conditions of reduced blood vessel patency, peripheral vascular disease, vascular disorders, such as Raynaud's disease, erectile dysfunction, sexual dysfunction, inflammatory diseases, heart attack, bronchitis, chronic asthma, allergic asthma, allergic rhinitis, glaucoma and diseases characterized by disorders of intestinal motility.

The compounds of formula (I) and their pharmaceutically acceptable salts, according to present invention, can be administered by any adequate route, for example, by oral, buccal, sublingual, rectal, vaginal, nasal, topical, intraperitoneal or parenteral routes. The preferred route is oral.

The pharmaceutical compositions comprising as active ingredient an effective amount of one of the derivatives of formula (I) can be presented in diverse types of pharmaceutical forms, such as, but not limited to: (i) tablet, optionally coated, chewable, effervescent, multilayered or soluble; (ii) pills; (iii) powder optionally dispersible or effervescent; (iv) capsules of any type, for example, hard gelatinous capsule, soft and amylaceous gelatinous capsule; (v) lozenges; (vi) granules, optionally in the form of microparticles or microcapsules, or vectorized preparations, for example, liposomes; (vii) suppositories, (viii) solutions optionally formulated for oral, nasal, ophthalmic use; (ix) injectable including subcutaneous, intradermic, intramuscular and intravenous; (x) suspensions; (xi) syrups; (xi) infusion; and others.

In case the pharmaceutical form is a solution or suspension for oral administration, the pharmaceutically acceptable vehicle can include solvents and co-solvents, buffers, preservatives, colorings, flavorings, sweeteners, reducing agents, thickening agents, sequestering agents, surfactants, substances to adjust pH (for example, chloric acid, sodium hydroxide), suspension agents, antioxidants, and others. Solvents or means of suspension can be purified water and/or other hydrophilic solvents (for example, ethanol, DMSO, propylene glycol, PEG) or hydrophobic solvents (for example, oils). The co-solvents can be ethanol, propylene glycol, glycerol, and others. The preservatives can be phenols, parabens, benzoic acid. The reducing agents can be vitamin E, ascorbic acid, etc. It is desirable that any of these excipients or additives are within the requirements of quality for pharmaceutical and veterinary use as established by competent authorities.

In the case the pharmaceutical form of the composition according to present invention is a tablet, it can include one or more excipients chosen from the group consisting of diluents, disintegrants, agglutinates, colorings and flavoring agents. Diluents can be one or more of calcium carbonate, calcium phosphate dibasic, calcium phosphate tribasic, calcium sulphate, microcrystalline cellulose, dextrates, dextrins, excipients of dextrose, fructose, kaolin, lactitol, lactose, manitol, sorbitol, starch, pregelatinized starch, sacarose, compressible sugar and confectioner's sugar, and in particular can be lactose. The agglutinate can one or more of methylcellulose, hydroxypropylcellulose, hydroxypropyl methylcellulose, polyvinylpirrolidone, gelatin, arabic gum, ethylcellulose, polyvinyl alcohol, pullulan, pregelatinized starch, agar, tragacanth, derivatives of alginic acid and propylene glycol, and alginate, and in particular can be polyvinylpirrolidone. The disintegrant can be one or more of low molecular weight substituted hydroxypropylcellulose, carboxymethyl cellulose, calcium carboxymethyl cellulose, sodium carboxymethyl cellulose, croscarmelose sodium, starch, sodium starch glycolate, crystalline cellulose, hydroxypropyl starch, and starch partially pre-gelatinized.

Solutions, suspensions or syrups for oral administration, for example, can be in pharmaceutical presentations of vials, flasks, and ampules.

The present invention also includes compositions of fast action, of extended action, and of delayed action. The preferred pharmaceutical forms of the invention are simple or uncoated tablets, coated tablets, and capsules.

The pharmaceutical compositions comprising as active ingredient an effective quantity of one of the derivatives of formula (I) can be presented with the referred derivative alone or in combination with another active ingredient.

The pharmaceutical compositions, as well as the medicament comprising as active ingredient an effective quantity of one of the derivatives of formula (I) have uses for the treatment and prevention of a large number of disorders, including stable, unstable and variant angina, hypertension, pulmonary hypertension, congestive heart failure, renal failure, arteriosclerosis, conditions of reduced blood vessel patency, peripheral vascular disease, vascular disorders, such as Raynaud's disease, erectile dysfunction, sexual dysfunction, inflammatory diseases, heart attack, bronchitis, chronic asthma, allergic asthma, allergic rhinitis, glaucoma and diseases characterized by disorders of intestinal motility.

For administration to warm blooded animals in the curative or preventative treatment of the disorders defined above, the oral doses of the compounds of formula (I) can be in the daily range of 0.1-900 mg for a patient in need. In practice, a doctor should determine the regime of unit doses most adequate for each patient, which depends on age, weight and individual response of the patient.

Examples of some oral pharmaceutical formulations comprising the compounds of formula (I) according to present invention are defined below.

EXAMPLE 4

| Coated tablet | | |
|---|---|---|
| | Quantity (mg) | % |
| Composition of the Core | | |
| Compound BL-122 | 1.000 | 1.25 |
| Microcristaline cellulose | 46.800 | 58.50 |
| Lactose monohydrate | 24.000 | 30.00 |
| Hydroxypropyl cellulose | 3.000 | 3.75 |
| Sodium croscarmellose | 2.000 | 2.50 |
| Magnesium stearate | 1.600 | 2.00 |
| Colloidal silicon dioxide | 1.600 | 2.00 |
| Composition of the Coating | | |
| Opadry Clear | 5.600 | 80.00 |
| Titanium Dioxide | 0.090 | 1.29 |
| Coloring | 0.010 | 0.14 |
| Talc | 1.300 | 18.57 |

EXAMPLE 5

| Coated tablet | | |
|---|---|---|
| | Quantity (mg) | % |
| Composition of the Core | | |
| Compound BL-122 | 2.500 | 3.05 |
| Microcristaline cellulose | 52.180 | 63.63 |
| Lactose monohydrate | 21.000 | 25.61 |
| Povidone | 1.200 | 1.46 |
| Sodium starch glycolate | 2.250 | 2.75 |
| Calcium stearate | 1.640 | 2.00 |
| Colloidal silicon dioxide | 1.230 | 1.50 |
| Composition of the Coating | | |
| Hypromellose | 5.380 | 71.77 |
| PEG 400 | 0.390 | 5.20 |
| Polysorbate 80 | 0.240 | 3.20 |
| Titanium dioxide | 0.090 | 1.20 |
| Coloring | 0.010 | 0.13 |
| Talc | 1.390 | 18.50 |

EXAMPLE 6

| Coated tablet | | |
|---|---|---|
| | Quantity (mg) | % |
| Composition of the Core | | |
| Compound BL-122 | 5.000 | 5.56 |
| Microcristaline cellulose | 39.370 | 43.74 |
| Lactose monohydrate | 28.800 | 32.00 |
| Corn starch | 11.700 | 13.00 |
| Povidone | 1.350 | 1.50 |
| Sodium croscarmellose | 2.070 | 2.30 |
| Magnesium stearate | 0.900 | 1.00 |
| Colloidal silicon dioxide | 0.810 | 0.90 |
| Composition of the Coating | | |
| Eudragit E 100 | 3.510 | 78.00 |
| PEG 6000 | 0.170 | 3.80 |
| Coloring | 0.015 | 0.30 |
| Titanium dioxide | 0.085 | 1.90 |
| Talc | 0.720 | 16.00 |

EXAMPLE 7

| Coated tablet | | |
|---|---|---|
| | Quantity (mg) | % |
| Composition of the Core | | |
| Compound BL-122 | 10.000 | 6.67 |
| Microcristaline cellulose | 132.500 | 88.33 |
| Crospovidone | 3.750 | 2.50 |
| Magnesium stearate | 2.250 | 1.50 |
| Colloidal silicon dioxide | 1.500 | 1.00 |
| Composition of the Coating | | |
| Eudragit E 100 | 4.650 | 77.45 |
| PEG 6000 | 0.190 | 3.20 |
| Coloring | 0.015 | 0.25 |
| Titanium dioxide | 0.095 | 1.60 |
| Talc | 1.050 | 17.50 |

EXAMPLE 8

| Coated tablet | | |
|---|---|---|
| | Quantity (mg) | % |
| Composition of the Core | | |
| Compound BL-122 | 20.000 | 8.00 |
| Microcristaline cellulose | 55.000 | 22.00 |

-continued

Coated tablet

|  | Quantity (mg) | % |
| --- | --- | --- |
| Lactose monohydrate | 158.250 | 63.30 |
| Hydroxypropyl cellulose | 7.500 | 3.00 |
| Sodium starch glycolate | 6.250 | 2.50 |
| Magnesium stearate | 3.000 | 1.20 |
| Composition of the Coating | | |
| Eudragit E 100 (35%) | 9.648 | 80.40 |
| Triethyl citrate | 0.516 | 4.30 |
| Titanium dioxide | 0.180 | 1.50 |
| Coloring | 0.036 | 0.30 |
| Magnesium silicate | 1.620 | 13.50 |

EXAMPLE 9

Simple tablet

| Composition | Quantity (mg) | % |
| --- | --- | --- |
| Compound BL-122 | 10.00 | 11.23 |
| Microcristaline cellulose | 73.38 | 82.45 |
| Sodium starch glycolate | 1.60 | 1.80 |
| Magnesium stearate | 1.60 | 1.80 |
| Colloidal silicon dioxide | 1.20 | 1.35 |
| Talc | 1.20 | 1.35 |
| Coloring | 0.02 | 0.02 |

EXAMPLE 10

Hard Gelatin Capsule

| Composition | Quantity (mg) | % |
| --- | --- | --- |
| Compound BL-122 | 10.00 | 10.00 |
| Lactose monohydrate | 83.00 | 83.00 |
| Methylcellulose | 1.20 | 1.20 |
| Sodium starch glycolate | 2.60 | 2.60 |
| Talc | 1.20 | 1.20 |
| Magnesium stearate | 2.00 | 2.00 |
| Hard gelatin capsule | 1 Capsule | 1 Capsule |

The techniques of preparation of these formulations are known by pharmacists, and known in the art.

The inhibitory activity of the compounds of the present invention was measured by means of in vitro analysis of the potency and efficacy of the relaxing effect of compound BL-122 on muscular tissue. The inhibitory effect of compound BL-122 on muscular relaxation was tested on cavernous body from rabbit and rat, as shown in Examples 11 and 12, respectively.

EXAMPLE 11

11.1. Isolation and Mounting of Preparations

Experiments used male rabbits weighing between 3.5 and 4.0 Kg. The animals were anesthetized with sodium pentobarbital (40 mg/kg, i.p), and the abdominal cavity opened for the withdrawal of the penis from the animals. The tissues were placed in a Petri dish containing Krebs-Henseleit solution pH 7.4 (NaCl 118 mM; KCl 4.8 mM; $CaCl_2$ 2.5 mM; $MgSO_4$ 1.2 mM; $KH_2PO_4$ 0.9 mM; $NaHCO_3$ 25 mM; glucose 11 mM) warmed to 37° C., and cartilage and adherent tissue were carefully removed. In general 3 segments containing approximately 2 cm of length of cavernous body were obtained from each animal. The preparations were mounted on glass reservoirs containing 5 ml of Krebs solution containing indomethacin (5.6 µM) at 37° C., continuously aerated with a mixture of 95% of $O_2$ and 5% of $CO_2$.

The preparations were submitted to a period of equilibrium of at least 90 minutes, under tension of 2 g, during which the bath solution was renewed each 15 minutes. Changes of isometric tension were registered using a TRI-201 force transducer (Letica Scientific Instruments, Spain) connected a polygraph.

11.2. Analysis of the Relaxing Effect of the Studied Compounds on Isolated Cavernous Body of Rabbit After the period of stabilization, the preparations were treated with single concentrations of 3 to 100M of phenylephrine. After the complete stabilization of the contractile responses to phenylephrine (about 5 minutes), the preparations were treated with increasing and cumulative concentrations (1 to 1000 nM) of each one of the tested compounds. After the complete relaxation of the tissues, the organs were washed multiple times with Krebs solution and rested for at least 60 minutes, before execution of a new dose response curve with the same compounds.

The relaxation responses caused by the compounds were calculated in relation to the contractile response of phenylephrine, which is considered as 100% of contraction.

Compound BL-122 was diluted in 10 mM of DMSO followed by serial dilution. To evaluate the effect of the utilized vehicle (DMSO), parallel control experiments were performed using the same volumes of the different dilutions of DMSO (vehicle).

The analysis of the relaxing effect on cavernous body of rabbit showed that addition of cumulative concentrations of 1 to 1000 nM of compound BL-122 promoted relaxation in the preparations of cavernous body previously treated with phenylephrine (3-10 nM), as illustrated in FIG. 1. The EC50 of compound BL-122 was 15.9 (1.8-29.9)µM, and the maximum relaxation (efficacy) was 63.1±7.8%. The control executed by means of treatment with vehicle demonstrated that it does not promote relaxation of aforementioned tissues.

EXAMPLE 12

12.1. Isolation and Mounting of Preparations

Experiments used male Wistar rats weighing between 300-350 g. The animals were maintained in an environment with humidity (60-80%) and controlled temperature (22±2° C.), with light-dark cycles of 12 hours and free access to water and rations. Before experiments, the animals were acclimatized in the laboratory for a minimum period of 1 hour. Each animal was used only one time in each test.

The animals were sacrificed by deepening anesthesia with ketamine and xylazine hydrochloride, followed by exsanguination made by section of the carotid artery. After opening of the thoracic cavity, the aorta was carefully removed and transferred to a Petri dish containing Krebs-Henseleit solution, with the following composition (mM): NaCl-118; KCl 4.7; $CaCl_2$ 2.5; $MgSO_4$ 1.2; $KH_2PO_4$ 0.9; $NaHCO_3$ 25; glucose 11. Afterwards, adipose and adjacent connective tissues were carefully removed.

The vessel was sectioned in the form of rings with approximately 3 to 4 mm of length, which were transferred to glass reservoirs with a total volume of 5 mL containing Krebs-Henseleit solution pH 7.4, maintained at 37° C., and continuously aerated with a mixture of 95% of $O_2$ and 5% of $CO_2$. Two metallic rods were inserted in their lumen, with one rod adapted to an isometric force transducer connected to a polygraph (TRI-201 Letica Scientific Instruments). The resting tension applied to the preparations corresponded to 1.0 g and the nutrient solution was substituted every 15 minutes.

After a period of equilibrium of 60 minutes, the preparations were treated with phenylephrine (0.3-1 µM), and after stabilization of the tonic contraction of the preparation, the integrity of the vascular endothelium was evaluated by the capacity of acetylcholine (ACh, 1 µM) to induce relaxation in the preparations. Only preparations that presented equal or greater than 75% relaxation were considered intact endothelium and, therefore, were selected for execution of experiments. Afterwards, the Krebs-Henseleit solution was replaced and followed by a period of equilibrium of 30 minutes.

12.2. Analysis of the Relaxing Effect of the Studied Compounds on Isolated Cavernous Body of Rat After the 30 minutes of rest, the preparations were treated with phenylephrine (0.3-1 µM) to stabilize tonic contractions, and dose response curves (DRC) for relaxation were performed using compound BL-122 (0.001-100 µM), in the presence of endothelium. Parallel experiments using only the solvent DMSO that was used to dilute compound BL-122 were performed on mounted tissues from the same animals.

Figure 2:
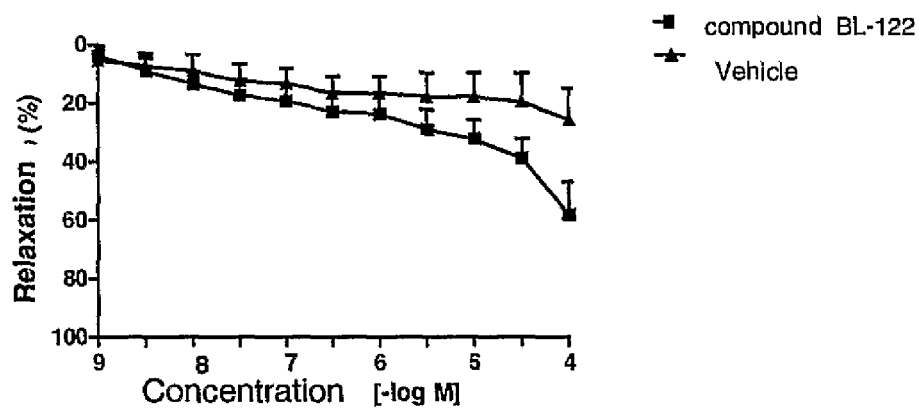
FIG. 2—dose response curve of the relaxing effect of compound BL-122 (a) and vehicle (b) on isolated aorta of rat.

The results illustrated in FIG. 2 show that the addition of cumulative concentrations of 1 to 1000 nM of compound BL-122 promoted relaxation in the preparations of rat aorta previously treated with phenylephrine.

The activity of compounds of the present invention on sexual behavior was measured by means of in vivo analysis of the efficacy of the effect of compound BL-122 on spontaneous erections, as shown in Example 13.

EXAMPLE 13

13.1. Isolation and Mounting of Preparations

The utilized protocol was adapted from literature articles (Hosseinzadeh et al., 2008; Rizzo et al., 2008). Two days before execution of experiments, couples of males and females were isolated in plastic boxes. In this period, males were housed for 1 hour per day in reinforced metal cages, rectangular with dimensions of 40×23×33 cm. On the day of the test, the male rats were treated with 10 mg/kg (oral) of compound BL-122 or only with vehicle (saline containing 10% of DMSO). Immediately afterwards, animals were placed in observation cages. The rats that received treatment by oral route were fasted for 4 hours before the test. One and a half (1.5) hours after the oral treatment, the females were placed with the respective males in the cages. The behavior of spontaneous erection was observed for 1 hour.

Figure 3:
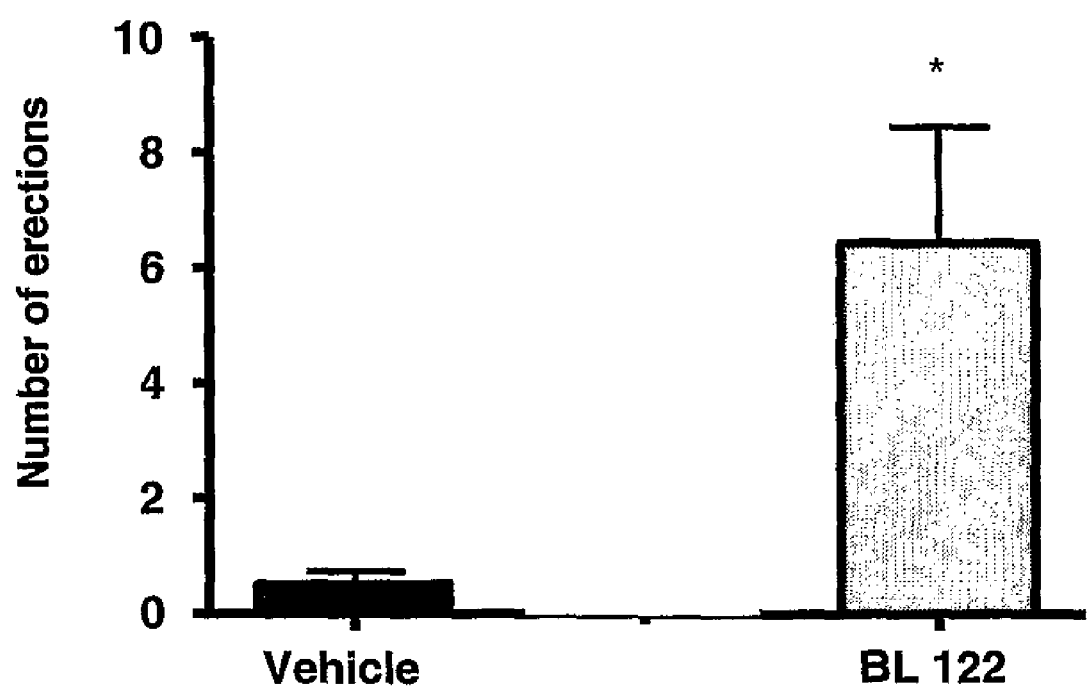
FIG. 3—test of sexual behavior in rats under the effect of compound BL-122 and vehicle (saline containing 10% of DMSO) administered by oral route, at the dose of 10 mg/kg. The utilized parameter regards spontaneous erections. The results are expressed as the average±SEM (standard error of the mean) of 9 animals. The statistical differences were evaluated using Analysis of Variance (ANOVA) followed by the Newman-Keuls test. P values less than 0.05 (P<0.05) were considered indicative of significance.

13.2. Effect of Compound BL-122 on the Sexual Behavior of Rats in the Presence of Females when Administered Orally The treatment by oral route with compound BL-122 at a dose of 10 mg/kg significantly increased the parameter regarding spontaneous erections when compared to the vehicle, about 6.4±2.0 as illustrated in FIG. 3.

The invention claimed is:

1. A compound of formula (I):

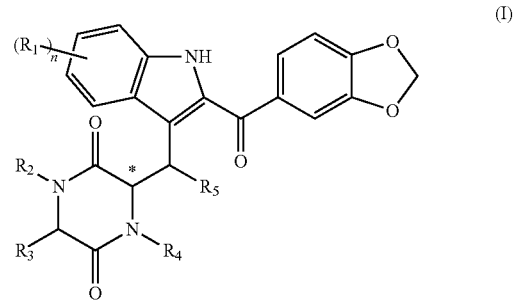

wherein, $R^1$ represents hydrogen, halogen, $C_{1-6}$ alkyl or O—R', where R' represents hydrogen or a lower alkyl;

n represents a number from 0 and 4;

$R^2$ represents hydrogen, $C_{1-6}$ alkyl, $C_{2-6}$ alkenyl, $C_{2-6}$ alkynyl, halo$C_{1-6}$alkyl, $C_{3-8}$ cycloalkyl, $C_{3-8}$ cycloalkyl$C_{1-3}$ alkyl, aryl $C_{1-3}$ alkyl or heteroaryl $C_{1-3}$ alkyl;

$R^3$ represents hydrogen, or $C_{1-3}$ alkyl or $R^2$ and $R^3$ together represent um 3- or 4-substituintes of um ring alkyl or alkenyl;

$R^4$ represents hydrogen, $C_{1-6}$ alkyl, $C_{2-6}$ alkenyl, $C_{2-6}$ alkynyl, halo$C_{1-6}$alkyl, $C_{3-8}$ cycloalkyl, $C_{3-8}$ cycloalkyl$C_{1-3}$ alkyl or heteroaryl $C_{1-3}$ alkyl;

$R_5$ represents hydrogen or O—R', where R' represents hydrogen or a lower alkyl;

or enantiomers or mixtures of enantiomers or a salt thereof.

2. An isomer of the compound of claim 1, wherein the isomer is chosen from compounds of formula (Ib):

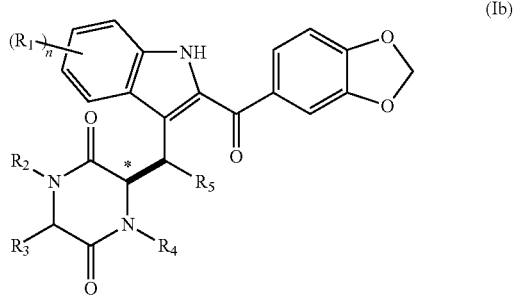

wherein,

* is a chiral carbon of R configuration;

$R^1$ represents hydrogen, halogen, $C_{1-8}$ alkyl or O—R', where R' represents hydrogen or a lower alkyl;

n represents a number from 0 and 4;

$R^2$ represents hydrogen, $C_{1-8}$ alkyl, $C_{2-6}$ alkenyl, $C_{2-6}$ alkynyl, halo$C_{1-6}$alkyl, $C_{3-8}$ cycloalkyl, $C_{3-8}$ cycloalkyl$C_{1-3}$ alkyl, aryl $C_{1-3}$ alkyl or heteroaryl $C_{1-3}$ alkyl;

$R^3$ represents hydrogen, or $C_{1-3}$ alkyl or $R^2$ and $R^3$ together represent um 3- or 4-substituintes of um ring alkyl or alkenyl;

$R^4$ represents hydrogen, $C_{1-6}$ alkyl, $C_{2-8}$ alkenyl, $C_{2-6}$ alkynyl, $C_{3-8}$ cycloalkyl, $C_{3-8}$ cycloalkyl$C_{1-3}$ alkyl, aryl $C_{1-3}$ alkyl or heteroaryl $C_{1-3}$ alkyl;

$R^5$ represents hydrogen or O—R', where R' represents hydrogen or a lower alkyl;

or an enantiomer or mixtures of enantiomers or a salt thereof.

3. An isomer of the compound of claim 1, wherein the isomer is chosen from compounds of formula (IC):

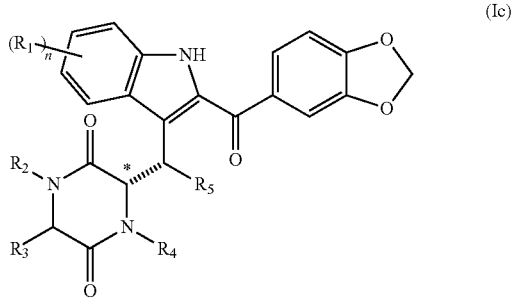

(Ic)

wherein,
* is a chiral carbon of S configuration;
$R^1$ represents hydrogen, halogen, $C_{1-6}$ alkyl or O—R', where R' represents hydrogen or a lower alkyl;
n represents a number from 0 and 4;
$R^2$ represents hydrogen, $C_{1-6}$ alkyl, $C_{2-6}$ alkenyl, $C_{2-6}$ alkynyl, $C_{3-8}$ cycloalkyl, $C_{3-8}$ cycloalkyl$C_{1-3}$ alkyl, aryl $C_{1-3}$ alkyl or heteroaryl $C_{1-3}$ alkyl;
$R^3$ represents hydrogen, or $C_{1-3}$ alkyl or $R^2$ and $R^3$ together represent um 3- or 4-substituintes of um ring alkyl or alkenyl;
$R^4$ represents hydrogen, $C_{1-6}$ alkyl, $C_{2-6}$ alkenyl, $C_{2-6}$ alkynyl, haloC$i\_6$alkyl, $C_{3-8}$ cycloalkyl, $C_{3-8}$ cycloalkyl$C_{1-3}$ alkyl, aryl $C_{1-3}$ alkyl or heteroaryl $C_{1-3}$ alkyl;
$R^1$ represents hydrogen or 0-R', where R' represents hydrogen or a lower alkyl;
or an enantiomer or mixtures of enantiomers or a salt thereof.

4. The compound according to claim 1, wherein $R^1$ represents hydrogen, $R^2$ represents $C_{1-6}$ alkyl and $R^3$ and $R^4$ represent hydrogen.

5. The compound according to claim 4, wherein the compound is 3-((2-(benzo[d][1,3]dioxol-5-carbonyl)-1H-indol-3-yl)methyl)-1-methylpiperazine-2,5-dione.

6. The compound according to claim 5, wherein the compound is (R)-3-((2-(benzo[d][1,3]dioxol-5-carbonyl)-1H-indol-3-yl)methyl)-1-methylpiperazine-2,5-dione.

7. The compound according to claim 5, wherein the compound is (S)-3-((2-(benzo[d][1,3]dioxol-5-carbonyl)-1H-indol-3-yl)methyl)-1-methylpiperazine-2,5-dione.

8. A pharmaceutical composition comprising one or more compounds according to claim 1, or pharmaceutical acceptable salts thereof, and a pharmaceutical acceptable excipient.

9. A medicament comprising one or more compounds according to claim 1, or pharmaceutically acceptable salts thereof.

* * * * *